(12) United States Patent
Naimer (10) Patent No.: US 6,573,419 B2
(45) Date of Patent: Jun. 3, 2003

(54) ELASTIC ADHESIVE WOUND DRESSING FOR CONTROL OF BLEEDING AND FOR DRESSING BLEEDING WOUNDS

(76) Inventor: Sody Naimer, 10 Haneshamot Hatehorot Street, 79 779 Neve Dkalim (IL)

( * ) Notice: Subject to any disclaimer, the term of this patent is extended or adjusted under 35 U.S.C. 154(b) by 0 days.

(21) Appl. No.: 09/845,711

(22) Filed: May 2, 2001

(65) Prior Publication Data

US 2002/0052570 A1 May 2, 2002

(51) Int. Cl.[7] .............................................. A61F 13/50
(52) U.S. Cl. ........................................ 602/41; 602/53
(58) Field of Search ..................... 602/44, 41; 523/111; 424/445–448

(56) References Cited

U.S. PATENT DOCUMENTS

| | | | | |
|---|---|---|---|---|
| 3,658,065 A | * | 4/1972 | Hirsch | 128/296 |
| 4,699,133 A | * | 10/1987 | Schafer et al. | 128/156 |
| 5,006,401 A | * | 4/1991 | Frank | 428/231 |
| 5,632,731 A | * | 5/1997 | Patel | 602/59 |
| 5,843,011 A | * | 12/1998 | Lucas | 602/57 |
| 5,939,339 A | * | 8/1999 | Delmore et al. | 442/149 |
| 5,981,822 A | * | 11/1999 | Addison | 602/41 |
| 6,043,406 A | * | 3/2000 | Sessions et al. | 602/41 |
| 6,274,787 B1 | * | 8/2001 | Downing | 602/41 |

* cited by examiner

Primary Examiner—Henry Bennett
Assistant Examiner—Nihir Patel
(74) Attorney, Agent, or Firm—G. E. Ehrlich Ltd.

(57) ABSTRACT

A compression dressing is disclosed. The compression dressing comprises a self-adhering elastic bandage strip designed for exerting a compressive force when wrapped around a body part sufficient to hold the compression dressing in place for a period of time to provide a therapeutic effect to a wound and an absorbent pad affixed to an inner side of a terminal portion or to a terminal end of the self-adhering elastic bandage strip.

23 Claims, 2 Drawing Sheets

ELASTIC ADHESIVE WOUND DRESSING FOR CONTROL OF BLEEDING AND FOR DRESSING BLEEDING WOUNDS

FIELD AND BACKGROUND OF THE INVENTION

The present invention relates to a wound dressing effective in rapidly controlling bleeding from a wound and, more particularly, to a wound dressing constructed and packaged such that the wound may be dressed using one hand.

Compression wound dressings: Bleeding control is a major consideration in the emergency treatment of acute trauma. Rapid and effective application of compression, at the scene of the traumatic incident until arrival at a medical facility, leads to decreased loss of blood from wounds and improves the chances of survival of the victim(s) (5, 6).

Traditional methods of bleeding control include direct compression, applied over the wound surface, usually employing an absorbent layer (4), and the tourniquet, tightly applied proximally to the wound (1). Direct compression is often effective in controlling bleeding, achieving high local pressures. Direct compression, however, is impractical in many emergency situations due to the need for continuous application by emergency care providers, thus neutralizing the care provider, denying performance of any other tasks. Direct compression cannot sustain the required constant local pressure, resulting in an increased tendency of the absorbent dressings to become saturated with blood (5). In addition, heavy direct compression may aggravate damage to other wounded tissues, such as fractures, and is inconvenient to apply over irregularly shaped or sensitive body parts.

The tourniquet, consisting of an elastic material bound tightly around the wounded body part, proximally to the wound, is applied with sufficient constricting force to cause ischemia distally to the site of application. This highly effective and widely used method of bleeding control may be left unattended, however, the induced ischemia is both extremely painful to the victim and commonly the cause of soft tissue and neurological damage to the distal body parts (1–3). Prevention of these undesired effects of tourniquet application is achieved by relieving the pressure at designated intervals, compromising the effectiveness and requiring additional attention by emergency care providers.

Elastic compression bandages: Elastic bandages, applied directly over the wound surface, are capable of providing significant compression and may be used in wound dressings. Elastic bandages are typically constructed of an elastomeric material, or a composite of elastic and non-elastic materials, which may be extended to provide constriction of the underlying surface. However, these fabric wraps, being non-adhesive, tend to shift with motion, compromising their comfort and compression capabilities, and therefore need to be fastened or bonded to an adhesive. Such wraps also lack absorbent qualities.

U.S. Pat. Nos. 3,575,782 and 4,984,584 to Hansen, and U.S. Pat. No. 4,699,133 to Schafer describe elastomeric, self-adhering compression bandages capable of achieving effective compression forces when applied over a dressed wound, but lacking absorbent properties.

Absorbent elastic wraps have been employed in compression bandages. U.S. Pat. No. 4,707,398 to Boggs, U.S. Pat. No. 4,720,415 to Vander Weilen, U.S. Pat. No. 5,230,701 to Meyer, and U.S. Pat. No. 4,957,795 to Reidel employ absorbent, elastic bandages which afforded both compression and exudate retention. However, the materials employed are non-self-adherent, requiring fastening and are prone to slippage when saturated with fluid.

An absorbent compression bandage has been proposed in which an insulated core comprises the major source of pressure. The core is embedded in absorbent material which becomes saturated with blood during application, and the dressing surface fails to adequately cover the wound surface. Thus, bleeding continues, requiring additional wound covering.

Another bandage comprises a rubber foam cushion and a pressure plate joined to the bandage surface. This bandage requires significant effort to apply, and results in diffuse compression and insufficient bleeding control.

In another design, a molded piece of polystyrene foam is centrally placed along a bandage surface, providing pressure on the outer surface of the bandage while the inner surface over the wound forms the area of contact. The molded plastic plate causes the bandage to protrude from the body surface and is exposed to possible erroneous displacement. The vacant space between the body surface and core, or mold, creates a potential for accumulation of unnoticed extravasated blood, dirt or fluids.

These and other configurations are disclosed in U.S. Pat. Nos. 2,858,830; 3,490,448; 3,888,247; 3,927,665; 3,625,209; 3,421,502; 4,005,709; and 4,377,159, and in BE 00522994 and GB00487743.

U.S. Pat. No. 5,939,339 to Delmore et al. describes a porous, elastic, self-adherent bandage flexibly attached to an absorbent layer. The self-adhering elastic is produced from elastic or spandex yarns bonded between porous fibrous webs or fabric, or a web of elastomeric polyurethane fibers. The absorbent layer covers all but a small portion of the elastic bandage's width along a major portion of the bandage's length. Thus, when applied, most of the absorbent pad is not in direct contact with the wound surface, and little self-adhesive bandage surface remains exposed, disposing the bandage to slippage and poor compression with movement and continued bleeding. A portion of the end of the elastic adhesive bandage remain uncovered by the absorbent layer, however in the event of dressing a wound not requiring the entire length of the bandage, the adhesive layer must be peeled back from the absorbent layer, a cumbersome and time-consuming inconvenience, especially for latex-gloved emergency care providers attending to trauma victims. Furthermore, the proposed bandage does not allow placement of the absorbent pad in a perpendicular orientation to the elastic bandage, encumbering the effective dressing of certain wounds, for example, a large longitudinal wound of a cylindrical body part (e.g., a limb). Another disadvantage of the proposed bandage is that the elastic, self-adherent component is composed of porous, opaque materials, covered by an absorbent layer, both precluding any observation of the wounded body part, or of the dressing after deployment. As depicted in the drawings, the proposed bandage requires two-handed application, while one-handed deployment, conceivably by the wounded victim himself, may provide a significant advantage in instances of severe trauma.

There is thus a widely recognized need for, and it would be highly advantageous to have a wound dressing effective in bleeding control devoid of the above limitations.

SUMMARY OF THE INVENTION

According to one aspect of the present invention there is provided a compression dressing, comprising (a) a self-adhering elastic bandage strip being designed for exerting a compressive force when wrapped around a body part sufficient to hold the compression dressing in place for a period of time to provide a therapeutic effect to a wound; and (b) an absorbent pad being affixed to an inner side of a terminal portion or to a terminal end of the self-adhering elastic bandage strip.

According to another aspect of the present invention there is provided a method of preparation and packaging of the compression dressing to enable rapid application within conditions of limited space, the method comprising (a) rolling the self-adhesive elastic bandage strip without affording contact between self-adherent surfaces; and (b) affixing the absorbent pad to the inner side of terminal portion or terminal end of said self-adhering elastic bandage strip.

According to still another aspect of the present invention the method of preparation and packaging of the compression dressing to enable application without direct contact of an applicator's gloved fingers or hand with an adhesive area, the method comprising rolling and packaging the self-adhering elastic bandage strip with its adhesive surface on an inner, unexposed side of a rolled self-adhering elastic bandage strip.

According to yet another aspect of the present invention there is provided a method of preparation and packaging of the compression dressing to enable easier application, the method comprising rolling and packaging the self-adhering elastic bandage strip with its adhesive surface on an outer, exposed side of a rolled self-adhering elastic bandage strip. In this case, a non-adhesive covering is provided for the exposed surface of the absorbent pad, and the adhesive properties of the self-adhering elastic bandage strip are selected so as not to adhere to, for example, latex gloves and/or adjacent surfaces of the packaging materials.

According to still another aspect of the present invention there is provided a method of application of the compression dressing over a wound in a body part, the method comprising (a) positioning the absorbent pad over the wound so as to effectively cover the wound; (b) orienting the self-adhering elastic bandage strip substantially in continuation or perpendicularly to a length of the absorbent pad covering the wound; and (c) wrapping the body part, covering at least the absorbent pad.

According to yet another aspect of the present invention there is provided a method of rapid application of the compression dressing over a wound in a body part, the method comprising (a) positioning the absorbent pad over the wound so as to effectively cover the wound; (b) rotating the rolled self-adhering elastic bandage strip 180 degrees around it's longitudinal axis, causing the self-adhesive surface to face outward; (c) orienting the self-adhering elastic bandage strip substantially in continuation or perpendicularly to a length of the absorbent pad covering the wound; and (d) wrapping the body part, covering at least the absorbent pad.

According to still another aspect of the present invention there is provided a method of application of the compression dressing over a longitudinal wound in a body part the longitudinal wound exceeding a width but not a length of said absorbent pad, the method comprising (a) positioning the absorbent pad over the longitudinal wound so as to effectively cover the longitudinal wound; (b) orienting said self-adhering elastic bandage strip substantially perpendicularly to a length of the absorbent pad covering the longitudinal wound; and (c) wrapping the body part, covering at least an entire length of absorbent pad.

According to yet another aspect of the present invention there is provided a method of application of the compression dressing to efficiently treat "entrance-exit" wounds, the method comprising positioning the absorbent pad over one of the wounds; applying additional absorbent pads over the second, opposite wound; and wrapping the body part with the self-adhering elastic bandage strip so as to achieve compression of the wound from both sides of the injured body part.

According to further features in preferred embodiments of the invention described below, the self-adhering elastic bandage strip is designed not to adhere to clothing, hair, skin or latex gloves.

According to yet further features in the preferred embodiments of the invention described below the self-adhering elastic bandage strip includes an elastomeric substrate layer and an adhesive layer joined thereto.

According to still further features in the described preferred embodiments the self-adhering elastic bandage strip is selected having self-adherence properties so as to allow unrolling of a roll of the elastic bandage strip without elastic extension of the elastic bandage strip.

According to yet further features in the described preferred embodiments the self-adhering elastic bandage strip is constructed so as to have self-adhesive properties sufficient to cause two adjacent layers of the compression dressing to remain adhered to one another under elastic extension without the use of a fastening mechanism.

According to still further features in the described preferred embodiments the self-adhering elastic bandage strip is constructed of a material including partially extended, longitudinally, vertically or irregularly extended elastic fibers bound to a fiber base to provide firm elastic extendibility in the longitudinal and vertical directions.

According to further features in the described preferred embodiments the self-adhering elastic bandage strip is constructed of a transparent material.

According to still further features in the described preferred embodiments the self-adhesive elastic bandage strip is constructed of non-woven elastomeric fibers and/or clear polyolefin polymer or copolymer films having firm elastic extendibility in longitudinal and vertical directions, and an adhesive, and having self-adhesive properties sufficient to cause two adjacent layers of the bandage to remain adhered to one another without the use of a fastening mechanism.

According to yet further features in the described preferred embodiments the films are printed polyolefin polymer or copolymer.

According to further features in the described preferred embodiments the self-adhesive elastic strip is constructed of clear polyolefin polymer or copolymer films coated with an extendable, self-adhesive finish sufficient to cause two adjacent layers of the bandage to remain adhered to one another without the use of a fastening mechanism.

According to further features in preferred embodiments of the invention described below, the absorbent pad is attached to the self-adhering elastic bandage strip by stitching, welding, needletacking and/or bonding.

According to still further features in the described preferred embodiments the adhesive is a natural rubber based adhesive or acrylic adhesive.

According to further features in preferred embodiments of the invention described below, the absorbent pad is constructed of foamed, woven or nonwoven material of natural or synthetic fibers selected from the group consisting of rayon, polyester, polyurethane, polyolefin, cellulose, cellulose derivatives, cotton, orlon and hydrogel polymeric materials.

According to still further features in the described preferred embodiments, the absorbent pad includes a coagulant.

According to further features in preferred embodiments of the invention described below, the compression dressing is rolled into a roll and packaged in a sterile package.

The present invention successfully addresses the shortcomings of the presently known configurations by providing a self-adhering elastic compression dressing, the large self-adhering surfaces providing superior compression and affording simple, rapid deployment of the rolled dressing over diversely shaped body parts. The dressing of the present invention requires minimal extension in deployment, and is therefore particularly suited for use in confined spaces and/or one-handed application. Effective control of bleeding is achieved by variable compression over the absorbent pad, which may include coagulant, and by the degree of constriction of peripheral circulation. Furthermore, when constructed of transparent material, the self-adhering elastic bandage strip allows for observation of continued bleeding.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of (i) an elastic, self-adhering, absorbent compression dressing, effective in preventing blood loss from wounds, (ii) methods of preparation and packaging the compression dressing and (iii) methods of application of the compression dressing over a wound.

The principles and operation of an elastic, self-adhering, absorbent compression dressing according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1:
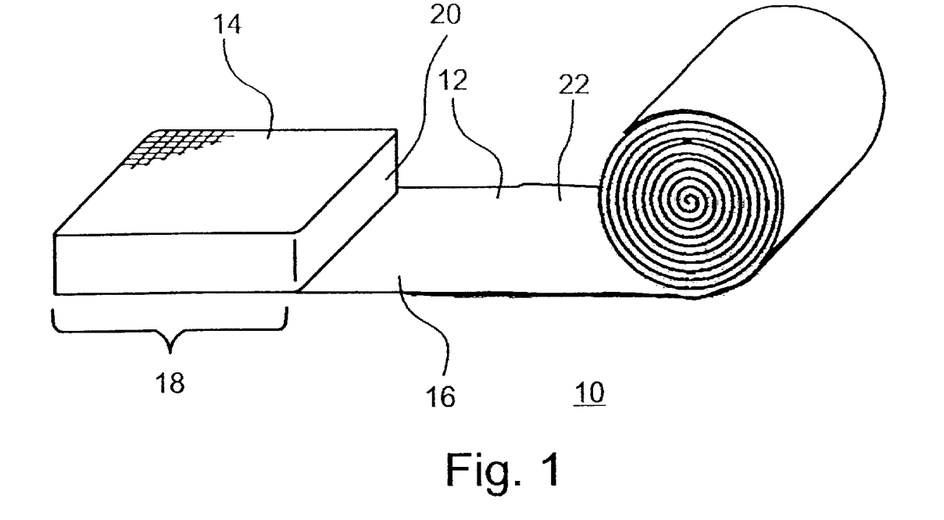
FIG. 1 is an overhead view of the partially deployed elastic adhesive dressing according to the present invention including a self-adhering elastic bandage strip, rolled up prior to its wrapping around an absorbent pad and a body part.
Figure 2:
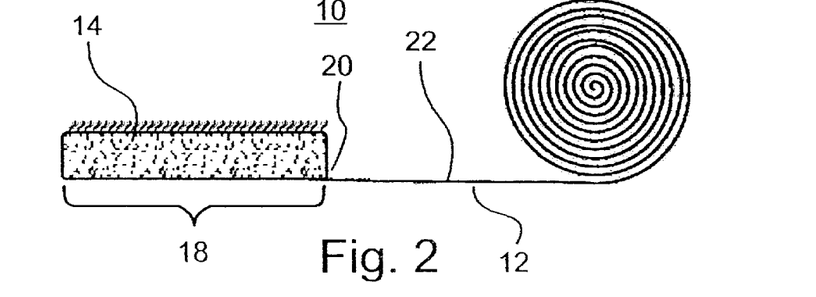
FIG. 2 is a cross-sectional view of the partially deployed elastic adhesive dressing shown in FIG. 1.
Figure 3:
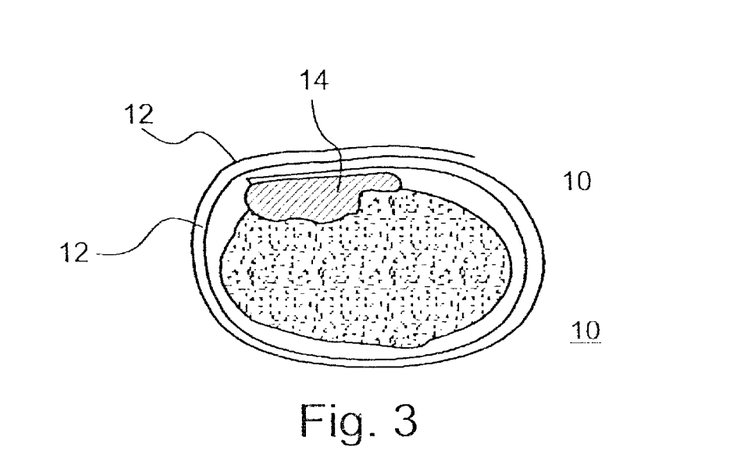
FIG. 3 is a cross-sectional view of the elastic adhesive dressing deployed over a wound on a cylindrical body part.

As shown in FIGS. 1–3, according to the present invention, there is provided a compression dressing which is referred to hereinbelow as dressing 10. Dressing 10 comprises a self-adhering elastic bandage strip 12. Strip 12 is designed for exerting a compressive force when wrapped around a body part, sufficient to hold the compression dressing in place for a period of time to provide a therapeutic effect to a wound. Dressing 10 further comprises an absorbent pad 14. Pad 14 is affixed to the inner side 16 of a terminal portion 18 or in the alternative to a terminal end 20 (shown in FIG. 1 as alternatives) of strip 12. A portion 22 of strip 12 which is not covered by absorbent pad 14 is adapted to directly contact a side of strip 12 opposite of absorbent pad 14 or a back side of strip 12 when dressing 10 is wrapped around the wounded body part. This contact allows dressing 10 to self-adhere. i.e., to adhere to itself, and prevents sliding or shifting of the wrap after it is in place, without the use of a fastening mechanism. For most of the length of strip 12, absorbent pad 14 does not cover strip 12 in order to provide a large, continuous contact area of the wrapped portion of strip 12.

Figure 4:
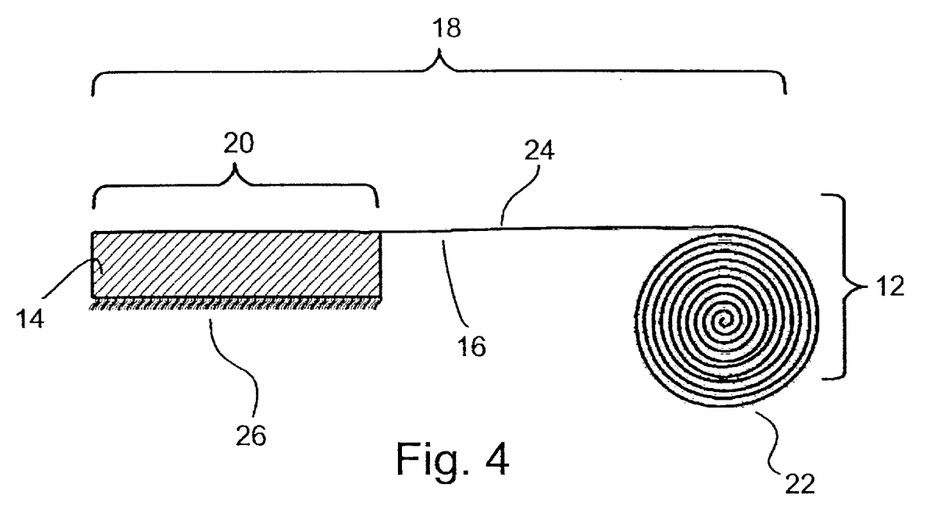
FIG. 4 is a cross sectional view of the partially deployed elastic adhesive dressing shown in FIG. 1, rolled to position the adhesive surface on the outer, exposed aspect of the self-adhering elastic strip.

As shown in FIG. 4 according to one preferred embodiment of the present invention, the adhesive side of the self-adhering elastic strip is positioned on the outer surface 24 of the dressing, and a non-adhesive covering 26 is provided for the exposed surface of the absorbent pad.

A preferred elastic bandage strip 12 according to the present invention will provide a compressive force of between about 1 to 180 mm Hg in practice actual pressures averaging about 80 mm Hg are exerted when wrapped around a body part. This pressure is generally sufficient to provide a therapeutic benefit without necessarily restricting arterial blood flow to the point of ischemia distal to the bandaged body part. A suitable method to measure compressive force for a wrap over a mock-wounded body part is described in the Examples section that follows. Therapeutic benefits provided by the present invention include control of bleeding, clot promotion, prevention of infection and approximation of wound surfaces. As is further demonstrated in the Examples section, the dressing of the present invention is applicable onto body regions unprotected by personal security equipment such as bullet proof vests and helmets, these include body locations where other compression dressings are inapplicable and/or ineffective. In addition, being devoid of a particular fastening mechanism other than self-adhesives, the compression dressing of the present invention is potentially readily self-applied by a single hand of an injured individual himself.

In a preferred embodiment of the present invention, the self-adhering elastic bandage strip is designed not to adhere to clothing, hair, skin or latex gloves.

In another preferred embodiment of the present invention the self-adhering elastic bandage strip is selected having self-adherence properties so as to allow unrolling of a roll of the elastic bandage strip without elastic extension of the elastic bandage strip.

In a preferred embodiment of the present invention, the self-adhering bandage strip is constructed so as to have self-adhesive properties sufficient to cause two adjacent layers of the bandage to remain adhered to one another without the use of a fastening mechanism.

Materials suitable for use in elastic bandage strip 12 of the present invention include materials which are elastic, conformable, provide adequate compression and which are self-adhering or which are made self adhering by the addition of an adhesion surface thereon. Materials which may be sterilized, including radiation sterilized, are preferred.

Thus, in one preferred embodiment of the present invention, the self-adhering bandage strip is constructed of partially extended, longitudinally, vertically or irregularly extended elastic fibers bound to a fiber base to provide firm elastic extendibility in the longitudinal and vertical directions.

In another preferred embodiment of the present invention, the self-adhering bandage strip is constructed of non-woven elastomeric fibers. Commercially available examples of elastic materials suitable for use in the present invention include woven bandages such as CUTTER-WRAP self-adhesive bandage (Cutter Animal Health, Miles Laboratories, Inc., Shawnee, Kans.), MEDI-RIP self-adherent bandage (Conco Medical Company, Bridgeport, Conn.) or SELF-GRIP sports tape/bandage (LMA, Ltd., South Norwalk, Conn.) and nonwoven bandages such as ROFLEX cohesive flexible bandage (Smith and Nephew Rolyan Inc., Menomonee Falls, Wis.), VET-FLEX veterinary flexible bandage (The Butler Company, Columbus, Ohio), CO-FLEX cohesive flexible bandage (Andover Coated Products, Inc., Marblehead, Mass.), FLEXUS support wrap (Kimberly-Clark Corporation Animal Care Division, Roswell, Ga.), COBAN self-adherent wrap (3M, St. Paul, Minn.), or EQUISPORT equine support Preferred materials for use in the elastic bandage strip of the present invention are COBAN self-adherent elastomeric bandage and EQUISPORT equine support bandage. COBAN is a self-adherent material which does not adhere to skin or hair and which does not traumatize skin during the bandage wear period. EQUISPORT equine support bandage is a self-adherent material related to COBAN elastomeric bandage except that it is able to provide a greater amount of compression when used. Methods suitable to make these self-adherent materials are reported in U.S. Pat. Nos. 3,575,782 to Hansen and U.S. Pat. No. 4,984,584 to Hansen et al., both of which are incorporated by reference as if fully set forth herein. The increased compression is a result of using greater numbers of larger elastic strands in the material. For example, a material having elastic strands of about 550–1, 700 denier and about 15–25 strands per inch is suitable.

A material made of melt blown microfiber webs may also be used in the strip of the present invention. The melt blown microfiber webs may be composed of a variety of well known thermoplastic elastomers including polyurethane, p, styrene-isoprene block copolymer, styrene-butadiene block copolymer, (KRATON polymer, Shell Oil Company, Belpre, Ohio) and blends of these elastomers with polyolefins such as polypropylene and polyethylene. In addition, the melt blown microfiber webs may include, but are not limited to, staple fibers, such as rayon, polyester, nylon, cotton, LANSEAL fiber, cellulose, or polypropylene fibers, to provide a blend of elastomeric and staple fibers.

In yet another preferred embodiment of the present invention the self-adhering elastic strip is constructed of a transparent material. Thus, the dressing allows monitoring of continued bleeding even when applied. Preferred materials are clear or printed polyolefin or copolymer films having firm extendibility in the longitudinal and vertical directions, and having self-adhesive properties. One such film that has been tested is a polyethylene film manufactured by Poleg Plastic Industries, Kibbutz Gevim, Israel, consisting of 54% low-density polyethylene (IPETHENE, Carmel Olefins Ltd., Haifa, Israel), 40% copolymer of ethylene and octene-1, and 6% SEBS-copolymer. This film has a thickness of 100 microns, modulus at 25% elongation of 0.6 (M.D.) and 0.5 (C.D.) Kg/mm$^2$, tensile strength of 2.0 (M.D.) and 2.8 (C.D.) Kg/mm$^2$, elongation at break of 600% (M.D.) and 1000% (C.D.), adhesion strength of 1600 gram/10 cm and adhesion to steel of 16.4 Newtons/inch. Another film which has been tested is AFFINITY* KC 8852 Polyolefin Plastomer (DOW Chemical, Horgen, Switzerland).

In another preferred embodiment the clear polyolefin polymer or copolymer film is coated with an extendable, self-adhesive finish. Thus, the self-adhering properties of polyolefin films may be enhanced by coating these materials with natural rubber latex or adhesives having low tack, providing greater adhesive properties while maintaining non-adherence to clothing, skin, hair or latex gloves. The latex or low tack adhesive is preferably coated onto one or both sides of the clear film in the amount of about 0.01–75 wt. % in order to provide for self-adherence or self-bonding when the strip is wrapped around a wound.

In a preferred embodiment of the present invention, the absorbent pad is attached to the self-adhering elastic bandage strip by an attaching method such as, but not limited to, stitching, welding, needletacking or bonding. Suitable adhesives which may be used to bind an absorbent pad to an elastic bandage strip of the present invention include pressure sensitive adhesives such as polyacrylates, polyvinylethers, and poly alpha-olefins, as well as polymers which may be formulated with appropriate tackifiers such as natural rubber, styrene-isoprene block copolymer, silicone rubber, cis-polyisoprene, styrene butadiene, and cis-polybutadiene, hot-melt adhesives such as low-density polyethylene, ethylene-vinyl acetate copolymers, ethylene-ethyl acrylate copolymers, paraffin waxes, polyesters, polyamides, polypropylene, styrene-butadiene block copolymers and polyurethanes, and curable adhesives such as silicones and urethanes. In addition, repositionable adhesives such as microsphere pressure sensitive adhesives may be used to bond the absorbent pad to the elastic bandage strip. Highly preferred adhesives would be those which are biocompatible with skin and which generally do not cause irritation or undesirable sensitivity reactions when in contact with skin for extended periods of time under normal conditions such as natural rubber and acrylate based adhesives.

In one embodiment of the present invention, the absorbent pad is constructed of foamed, woven or non-woven material of natural or synthetic fibers, such as, but not limited to, rayon, polyester, polyurethane, polyolefin, cellulose, cellulose derivatives, cotton, orlon or hydrogel polymeric materials. Preferably, the absorbent material both absorbs wound exudate and protects the wound by absorbing shocks. Other types of materials having similar absorbent properties and characteristics would also be suitable for use in this invention. Examples of absorbent materials are dacron-polyester cast padding MW0.4, (3M, St. Paul, Minn.), DELTA-ROL acrylic cast padding 6884, (Johnson & Johnson, New Brunswick, N.J.), SOF-ROL 100% needle-tacked rayon cast padding HRI 8137-009034, (Johnson & Johnson, New Brunswick, N.J.), SPECIALIST cotton cast padding HRI 8137-009044 (Johnson & Johnson, New Brunswick, N.J.), WEBRIL cotton undercast padding 3175 (The Kendall Company, Boston, Mass.), WEBRIL II cotton undercast padding 4221 (The Kendall Company, Boston, Mass.), nonwoven cotton web 142-451 and nonwoven rayon/polyester web 140-037 (VeraTec Company, Wapole, Mass.), and an absorbent resilient open-cell foam such as polyurethane, polyester, polyether, polyolefin foams as described in U.S. Pat. No. 3,908,645 to Sandvig.

Other suitable absorbent materials include composite materials such as nonwoven polymeric matrices combined with highly hydrophilic fluid absorbing materials. Highly hydrophilic fluid absorbing materials include polymeric absorbent fibers or particles, such as, but not limited to, modified polysaccharides, modified polyurethanes and high molecular weight acrylic polymers containing hydrophilic groups. A preferred highly hydrophilic fluid absorbing material is acrylonitrile fibers treated with alkali metal hydroxides. A commercially available hydrogel polymeric material is distributed under the tradename LANSEAL fiber (Japan Exlan Co., Ltd., Osaka, Japan). These types of composite absorbent materials are readily prepared using well known methods such as the method reported in U.S. Pat. No. 4,957,795 to Riedel.

Typically, the absorbent material includes one or more layers of a nonwoven, melt blown absorbent fiber which provides loft to the material and which absorbs liquids. The surface of the absorbent material which contacts the wound may additionally be treated or modified so that it will not adhere to the wound. For example, the absorbent material may be covered with a variety of commercially available wound contact materials such as TEGAPORE woven nylon web, TEGADERM polyurethane film or TEGASORB hydrocolloid (all available from 3M, St. Paul, Minn.) as well as other well known related materials. Preferably, the absorbent pad includes a coagulant, enhancing clot formation in the wound and improving bleeding control properties of the compression dressing.

As used herein in the specification and in the claims section that follows, the term "coagulant" is defined as any agent that promotes clotting, or coagulation of blood, which may be safely applied to an open wound. A non-limiting example of such a coagulant material comprising gelatin, thrombin and calcium is described in U.S. Pat. No. 6,045,570 to Epstein, et al.

In another preferred embodiment of the present invention the compression dressing is rolled into a roll and packaged in a sterile packaging. The dressing may be sterilized by, for example, exposure to heat, radiation or gas.

According to another aspect of the present invention, there is provided a method of preparation and packaging of the compression dressing of the invention to enable rapid application within conditions of limited space, the method is effected by rolling the self-adhesive elastic bandage strip without affording contact between self-adherent surfaces, and affixing the absorbent pad to the inner side of the terminal portion or to the terminal end of the self-adhering bandage strip. It will be appreciated in this respect that, standard issue military ("first-aid") wound bandages, constructed with the absorption pad in the center of fastening strings, for example, must be spread open and extended to achieve desired wound coverage and compression, making their use in confined space awkward and ineffective.

According to yet another aspect of the present invention there is provided a method of preparation and packaging of the compression dressing to enable easier application. This method is effected by rolling and packaging the self-adhering elastic bandage strip with its adhesive surface on an outer, exposed side 24 of a rolled self-adhering elastic bandage strip. In this case, a non-adhesive covering 26 is provided for the surface of the absorbent pad, and the adhesive properties of the self-adhering elastic bandage strip are selected so as not to adhere to, for example, latex gloves and/or packaging materials, the advantages being, easier application.

When prepared and packaged in the above mentioned manners, the compression dressing of the may be unwound and wrapped while still in rolled form, within a confined space around a wounded body part, affording more rapid and effective treatment in emergency and trauma situations.

According to a further aspect of the present invention there is provided a method of application of the compression dressing of the invention over a wound in a body part. The method according to this aspect of the present invention is effected by positioning the absorbent pad over the wound so as to effectively cover the wound; orienting the self-adhering elastic bandage strip substantially in continuation or perpendicularly to a length of the absorbent pad covering the wound and wrapping the body part, covering at least the absorbent pad. Additionally, and alternatively, there is provided a method of rapid application of the compression dressing of the invention over a wound in a body part, the method effected by positioning absorbent pad 14 over the wound so as to effectively cover the wound; orienting the self-adhering elastic bandage strip substantially in continuation or perpendicularly to a length of the absorbent pad covering the wound; rotating the rolled self-adhering elastic bandage strip 12 180 degrees around it's longitudinal axis, causing the self-adhesive surface to face outward; and wrapping the body part, covering at least the absorbent pad. When applied in this manner, the outward-facing orientation of the self-adhering surface allows for greater tension and more effective compression over the wounded body part.

In yet another aspect of the present invention, there is provided an efficient method for dressing "entrance-exit wounds". It will be appreciated, in this context, that a body part, such as a limb, may sustain wounds on opposite surfaces resulting from penetration injuries, for example, gunshot wounds. The addition of absorbent pad or pads to the wound opposite (e.g. the "exit" wound) the absorbent pad of the compression dressing (e.g. covering the "entrance" wound), and compression of both wounds with the same self-adhering elastic bandage strip allows for rapid and efficient dressing and bleeding control of these often difficult-to-manage trauma.

The compression dressing of the invention may be easily applied by untrained personnel or even, in some instances by the injured individual himself. The dressing is not intended to absorb large amounts of blood, but allows hygienic isolation of the area and prevents excess bleeding by sealing the wounded region and compressing and thereby blocking ruptured blood vessels. Superior compression of the wounded body part is achieved by reduction of space between the elastic strip and the wound, the degree of compression determined by altering the amount of extension and tightening of the bandage during wrapping as chosen at the discretion, and according to the experience, of the applicator. Thus, the compression dressing of the present invention affords a wide range of possible pressures, as may suit demands, from moderate adherence in treating, for example, flesh wounds or burns, to complete obstruction of local and distal circulation, as in deep wounds with severe arterial bleeding.

According to still a further aspect of the present invention there is provided a method of application of the compression dressing of the invention over a longitudinal wound in a body part, the longitudinal wound exceeding a width but not a length of the absorbent pad. The method according to this aspect of the present invention is effected by positioning the absorbent pad over the longitudinal wound so as to effectively cover the wound; orienting the elastic bandage strip substantially perpendicularly to a length of the absorbent pad covering the wound; and wrapping the body part, covering at least an entire length of the absorbent pad.

It will be appreciated in this respect that other compression dressings, such as the standard military bandage, cannot be easily deployed along the length of a limb, for example. Thus, the effective dressing of a large longitudinal wound in a limb, for example, requires opening and application of more than one bandage of this kind. By simply turning the elastic bandage strip of the present invention perpendicular to the absorbent pad before wrapping, longitudinal wounds up to the entire length of the absorbent pad may be quickly and effectively treated.

Additional objects, advantages, and novel features of the present invention will become apparent to one ordinarily skilled in the art upon examination of the following example, which is not intended to be limiting. Additionally, each of the various embodiments and aspects of the present invention as delineated hereinabove and as claimed in the claims section below finds experimental support in the following example.

EXAMPLE

Comparative Evaluation of Elastic Adhesive Dressing and Other Compression Techniques Under Simulated Field Conditions

Materials and Experimental Methods

Compression techniques: Compression was achieved by the elastic adhesive dressing and two traditionally employed techniques, direct manual compression and the military bandage.

Elastic adhesive dressing: In this study the elastic adhesive dressing consisted of an "ace-bandage" with adhesive properties, either COBAN™, (3M Health Care Co., St. Paul, Minn., U.S.A.), normally used for post-surgical wound covering or PEG™ brand (Becton Dickinson Co., New Jersey, U.S.A.), combined with an eccentric, non-adhesive, absorbent contact pad. In order to judge whether a rigid, protruding body enhances pressure where the elastic adhesive dressing failed to reach satisfactory pressures, a 5×5× 2.5 cm block of wood or rigid plastic was inserted into the external aspect of the contact pad, the elastic adhesive bandages sealed above the addition.

Direct manual compression: Manual compression was achieved using a military bandage opened over the hypothetically wounded area (4).

Military bandage: Standard issue military bandage was applied according to published guidelines (5), with strings tied as taut as possible.

Hypothetically wounded body regions: The body regions chosen for assessment were those amenable to compression and representative of diverse body surfaces. The regions overlying abdominal viscera and ribcage were excluded. All teams bandaged upper arm, thigh, scalp and the groin area. Optional locations were: lateral neck, shoulder (proximal aspect), axilla and the stump of a below-the-knee amputation.

Pressure measurement: Individual pressure measurements were recorded for each body region using a pressure gauge comprising (a) an airbladder from a blood pressure cuff for premature infants; and (b) an accurate pressure sensor or transducer (Model DP-Y27, Sunx registered Trade Company) acting as a manometer, registering the pressure (in kilopascals or mm Hg) generated on a LED monitor.

One of the study participants was appointed as the leading member of each team, responsible for recording pressures at designated intervals and overseeing the adherence to study guidelines. After near-maximal inflation of the air bladder, the gauge is calibrated to zero, the bladder is positioned over the test region, and fastened by adhesive strips. The Emergency Care Provider is directed to act as if treating active hemorrhaging from the area with one of the compression techniques: At the signal "GO" the Emergency Care Provider removes the dressings from their packaging, begins dressing the imaginary wound and upon completion signals by lifting his hands from the body of the simulated victim. Recordings were made of (a) pressure at conclusion of dressing; and (b) pressure fluctuations (if noted) over a seven minute period, at half-minute or one minute intervals. Where pressure remained constant over three minutes recording was concluded.

Additional parameters: Simulated patients reported their subjective sensation of pain and discomfort resulting from the compression technique using an analog scale. The Emergency Care Providers reported their assessment of ease of use and overall satisfaction with each compression technique. Time to completion of each compression technique was recorded by the team leader for each experiment.

Participants: Four teams from various ranges of field experience participated in the study: a veteran trauma team employed in a rural, relatively trauma-stricken security zone; a crew from a major urban area; a military medical unit well trained in care of the wounded but lacking extensive practical experience; and a group of first aid volunteers trained through standard courses. The teams provided the volunteers serving as "mock wounded victims" to be treated. The same volunteer continued through assessment of all techniques for bleeding control for one specified anatomical location, allowing subjective comparisons between the techniques. The Emergency Care Provider also administered all three techniques to each anatomical location, to allow for accurate comparisons. All participants were unpaid volunteers.

Preparation of the teams consisted of an explanation, and single demonstration of each technique prior to the commencement of the experiments.

Interpretation of data: Data from the participant's questionnaires was entered on epi-info 6.01 and analyzed using SSPS statistical package.

Experimental Results

Elastic adhesive dressing provides superior compression: A total of sixty-eight experiments, encompassing the compulsory, and some optional anatomical locations, were performed by the four teams. Comparison of the average, and consistency of pressures generated by each of the techniques demonstrates the superiority of compression using the elastic adhesive dressing (average 88 mm Hg; range equals 44–120 mm Hg) over the traditional military bandage (average 33 mm Hg; range equals 0.82–65 mm Hg). The advantage of the elastic adhesive dressing over the military bandage was most obvious when tested on difficult-to-dress body parts such as the groin (self-adhering elastic dressing: 34.1 mm Hg pressure; military bandage: 17.5 mm Hg pressure), the scalp (self-adhering elastic dressing:

122.46 mm Hg pressure; military bandage: 15.63 mm Hg pressure) and an amputee's stump (self-adhering elastic dressing: 73.93 mm Hg pressure; military bandage: 8.5 mm Hg pressure). Both bandages provided less pressure than manual compression (average 180 mm Hg; range equals 130–230 mm Hg). Where target pressures could not be achieved the addition of a rigid body to the elastic adhesive dressing did not provide any advantage.

Elastic adhesive dressing is rapidly and easily applied: Comparing the recorded times from removal from packaging, to completion of desired compression, there was a small but consistent (6–48 seconds) advantage in application times for the military bandage compared with the elastic adhesive dressing when applied on most anatomical areas tested. However, this was not reflected in the overall satisfaction ratings.

Reports of overall satisfaction by both the Emergency Care Providers, and the mock wounded victims indicated a clear preference for the elastic adhesive dressing (average satisfaction rating 8.7/10) over both the military bandage (average satisfaction rating 4.8/10) and manual pressure (average satisfaction rating 6.8/10). This advantage was further emphasized by the enthusiastic requests for samples of the elastic adhesive dressing from all the study's participants (samples were not distributed).

Durability of COBAN™ roll compared to PEG™: During the course of experimentation, the COBAN™ roll tore while being stretched, requiring an additional unit of adhesive elastic to be applied in order to achieve target compression values. This occurred over the scalp, thigh and groin regions. Thereafter, the PEG brand roll was deployed over these regions. The Emergency Care Providers noted that the PEG brand roll was somewhat more difficult to open and wrap over the wounded surface than the COBAN™ roll.

Thus the elastic adhesive dressing provides a rapid, convenient, easily applied method of bleeding arrest achieving superior compression when deployed over diverse anatomical regions.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiment thereof, it is evident that many alternatives, may and will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

List of Reference Cited

Additional References are cited within the Text

1. Klenerman L., Biswas M., Hulands G H, Rhodes A M. Systemic and local effects of the application of a tourniquet. J. Bone Joint Surgery 1980; 63B:385–8
2. Walfin G., Raik S., Walid S., Greemberg B., Daniel M. Limb nerve paralysis in a combat soldier wound following the use of a tourniquet. Harefua 1999; 139:352–5.
3. Klenerman L. Tourniquet paralysis (editorial). J Bone Joint Surgery 1983; 65B: 374–5.
4. Buntain W. L., ed. Management of Pediatric Trauma. Philadelphia, Pa: WB Saunders Co.: 1995, 80–1.
5. Asensio J A., Barton J M., Wonsetler M S N, Thomford N R. Trauma: a systemic approach to management. Am Fam Phys 1988; 38: 97–111.
6. Shock and resuscitation. In Kirby, N G., and Blackburn, G., eds. Field Surgery Pocket Book, London, Her Majesty's Stationary Office; 1981. 34–49.

What is claimed is:

1. A compression dressing, comprising:
   (a) an elongated, self-adhering elastic bandage strip; and
   (b) an absorbent pad being of substantially lesser length than said self-adhering elastic bandage strip, said absorbent pad being affixed to a terminal end of said self-adhering elastic bandage strip; said elastic bandage strip being designed, and of sufficient length, such that said absorbent pad may be applied to a wound on a body part, and the remainder of said strip or portion thereof, may be wrapped around said absorbent pad and said body part to hold the compression dressing in place and to exert a compressive force on the wound for a period of time to permit a therapeutic effect to the wound.

2. The compression dressing of claim 1, wherein said self-adhering elastic bandage strip is designed not to adhere to clothing, hair, skin or latex gloves.

3. The compression dressing of claim 1, wherein said self-adhering elastic bandage strip includes an elastomeric substrate layer and an adhesive layer adhered thereto on one surface thereof, said absorbent pad being affixed to a non adhesive surface of said elastic bandage strip at said terminal end thereof.

4. The compression dressing of claim 1, wherein said self-adhering elastic bandage strip is selected having self adherence properties so as to allow unrolling of a roll of said self-adhering elastic bandage strip without elastic extension of said elastic bandage strip.

5. The compression dressing of claim 1, wherein said self-adhering elastic bandage strip is constructed so as to have self-adhesive properties sufficient to cause two adjacent layers of the compression dressing to remain adhered to one another under elastic extension without the use of a fastening mechanism.

6. The compression dressing of claim 1, wherein said self-adhering elastic bandage strip is constructed of a material including partially extended, longitudinally, vertically or irregularly extended elastic fibers bound to a fiber base to provide firm elastic extendibility in the longitudinal and vertical directions.

7. The compression dressing of claim 1, wherein said self-adhering elastic bandage strip is constructed of a transparent material.

8. The compression of claim 1, wherein said elastic bandage strip is constructed of non-woven elastomeric fibers having firm elastic extendibility in longitudinal and vertical directions, and an adhesive, and having self-adhesive properties sufficient to cause two adjacent layers of the bandage to remain adhered to one another without the use of a fastening mechanism.

9. The compression dressing of claim 1, wherein said self-adhering elastic bandage strip is constructed of clear polyolefin polymer or copolymer films having firm elastic extendibility in the longitudinal and vertical directions, and having self-adhesive properties sufficient to cause two adjacent layers of said self-adhering elastic bandage strip to remain adhered to one another without the use of a fastening mechanism.

10. The compression dressing of claim 9, wherein said films are printed polyolefin polymer or copolymer films.

11. The compression dressing of claim 1, wherein said self-adhesive elastic bandage strip is constructed of a clear polyolefin polymer or copolymer film coated on one surface with an extendable, self-adhesive adhesive effective to cause two adjacent layers of said self-adhering elastic bandage strip to remain adhered to one another without the use of a fastening mechanism.

12. The compression dressing of claim 1, wherein said absorbent pad is affixed to said self-adhering elastic bandage strip by an affixing method selected from the group consisting of stitching, welding, needletacking and bonding.

13. The compression dressing of claim 12, wherein said bonding is effected by an adhesive selected from a group consisting of natural rubber based adhesives and acrylic adhesives.

14. The compression dressing of claim 1, wherein said absorbent pad is constructed of foamed, woven or nonwoven material of natural or synthetic fibers selected from the group consisting of rayon, polyester, polyurethane, polyolefin, cellulose, cellulose derivatives, cotton, orlon and hydrogel polymeric materials.

15. The compression dressing of claim 1, wherein said absorbent pad includes a coagulant.

16. The compression dressing of claim 1, rolled into a roll and packaged in a sterile packaging.

17. A method of preparation and packaging of the compression dressing of claim 1 to enable rapid application within conditions of limited space, the method comprising:
   (a) rolling said self-adhesive elastic bandage strip without affording contact between self-adherent surfaces; and
   (b) affixing said absorbent pad to said inner side of said terminal portion or to said terminal end of said self-adhering elastic bandage strip.

18. A method of preparation and packaging of the compression dressing of claim 1 to enable application without direct contact of an applicator's gloved fingers or hand with an adhesive area, the method comprising rolling and packaging said self-adhering elastic bandage strip with its adhesive surface on an inner, unexposed side of a rolled self-adhering elastic bandage strip.

19. A method of application of the compression dressing of claim 1 over a wound in a body part, the method comprising:
   (a) positioning said absorbent pad over the wound so as to effectively cover the wound;
   (b) orienting said self-adhering elastic bandage strip substantially in continuation or perpendicularly to a length of said absorbent pad; and
   (c) wrapping the body part, covering at least said absorbent pad.

20. A method of application of the compression dressing of claim 1 over a longitudinal wound in a body part, the longitudinal wound exceeding a width but not a length of said absorbent pad, the method comprising:
   (a) positioning said absorbent pad over the longitudinal wound so as to effectively cover the longitudinal wound;
   (b) orienting said self-adhering elastic bandage strip substantially perpendicularly to a length of said absorbent pad covering the longitudinal wound; and
   (c) wrapping the body part, covering at least an entire length of said absorbent pad.

21. A method of preparation and packaging of the compression dressing of claim 1, the method comprising rolling and packaging said self-adhering elastic bandage strip with its adhesive surface on an outer, exposed side of a rolled self-adhering elastic bandage strip, and providing a nonadherent layer on the surface of said absorbent pad.

22. A method of rapid application of the compression dressing of claim 1 over a wound in a body part, the method comprising:
   (a) positioning said absorbent pad over the wound so as to effectively cover the wound;
   (b) rotating the rolled portion of said self-adhering elastic bandage strip 180 degrees around it's longitudinal axis;
   (c) orienting said self-adhering elastic bandage strip substantially in continuation or perpendicularly to a length of said absorbent pad covering the wound; and
   (d) wrapping the body part, covering at least said absorbent pad.

23. A method of application of the compression dressing of claim 1 to efficiently treat "entrance-exit" wounds, the method comprising positioning said absorbent pad over one of the wounds, applying additional absorbent pads over the second, opposite wound, and wrapping the body part with said self-adhering elastic strip so as to achieve compression of the wound from both sides of the injured body part.

* * * * *